United States Patent
De Souza et al.

(10) Patent No.: US 7,381,242 B2
(45) Date of Patent: Jun. 3, 2008

(54) TREATMENT OF HYDROGEN/HYDROCARBON MIXTURES ON ADSORBENTS REGENERATED AT HIGH PRESSURE

(75) Inventors: Guillaume De Souza, Issy les Moulineaux (FR); Pascal Tromeur, Cercottes (FR)

(73) Assignee: L'Air Liquide Société Anonyme á Directoire et Conseil de Surveillance pour l'Etude et l'Exploitation des Procédés Georges Claude, Paris (FR)

( * ) Notice: Subject to any disclaimer, the term of this patent is extended or adjusted under 35 U.S.C. 154(b) by 172 days.

(21) Appl. No.: 10/504,454

(22) PCT Filed: Feb. 5, 2003

(86) PCT No.: PCT/FR03/00350

§ 371 (c)(1),
(2), (4) Date: Mar. 21, 2005

(87) PCT Pub. No.: WO03/070357

PCT Pub. Date: Aug. 28, 2003

(65) Prior Publication Data

US 2005/0172803 A1    Aug. 11, 2005

(30) Foreign Application Priority Data

Feb. 15, 2002    (FR)    .................................. 02 01919

(51) Int. Cl.
*B01D 53/047*    (2006.01)
*C01B 3/56*    (2006.01)
*C07C 7/12*    (2006.01)

(52) U.S. Cl. ............................... 95/95; 95/143; 95/148

(58) Field of Classification Search ............ 95/95–106, 95/143, 144, 147, 148, 900, 901, 902; 96/132; 423/248, 648.1
See application file for complete search history.

(56) References Cited

U.S. PATENT DOCUMENTS

| | | | |
|---|---|---|---|
| 3,365,859 A | * | 1/1968 | Sandberg ..................... 95/105 |
| 4,964,888 A | * | 10/1990 | Miller ........................... 95/95 |
| 5,234,472 A | * | 8/1993 | Krishnamurthy et al. ...... 95/98 |
| 5,250,088 A | * | 10/1993 | Yamaguchi et al. ........... 95/98 |
| 5,912,422 A | | 6/1999 | Bomard et al. |
| 6,210,466 B1 | * | 4/2001 | Whysall et al. ............... 95/100 |
| 6,402,813 B2 | * | 6/2002 | Monereau et al. ............. 95/96 |
| 6,425,939 B1 | | 7/2002 | Moreau et al. |

(Continued)

FOREIGN PATENT DOCUMENTS

DE    26 24 346    12/1977

(Continued)

OTHER PUBLICATIONS

International Search Report for PCT/FR 03/00350.

*Primary Examiner*—Frank M Lawrence
(74) *Attorney, Agent, or Firm*—Elwood L. Haynes

(57) ABSTRACT

A method of PSA gas separation for a gas mixture containing hydrogen and hydrocarbon impurities. The gas mixture is put in contact with silica gel and activated carbon so as to adsorb the impurities in the gas mixture. Hydrogen rich and waste gas flows are produced. The waste gas flow may be sent to the combustible network of a petrochemical site, without having to make a pressure adjustment to the waste gas.

25 Claims, 1 Drawing Sheet

U.S. PATENT DOCUMENTS 6,483,001 B2 * 11/2002 Golden et al. .............. 585/820
2002/0010093 A1    1/2002 Monereau et al.
2002/0014153 A1 *  2/2002 Baksh et al. .................. 95/96

FOREIGN PATENT DOCUMENTS

| | | | |
|---|---|---|---|
| EP | 1 076 035 A2 | 2/2001 | |
| EP | 1 095 701 A1 | 5/2001 | |
| EP | 1 132 341 A1 | 9/2001 | |
| WO | WO 97 45363 | 12/1997 | |

* cited by examiner

TREATMENT OF HYDROGEN/HYDROCARBON MIXTURES ON ADSORBENTS REGENERATED AT HIGH PRESSURE

BACKGROUND

The present invention relates to a PSA (Pressure Swing Adsorption) method for separating a gas mixture containing hydrogen ($H_2$) and hydrocarbon type ($C_nH_m$) impurities, in which the gas mixture to be purified is contacted with an activated charcoal and silica gel in order to adsorb the impurities present in the gas mixture to be treated, and to produce a hydrogen-rich stream, and further to produce a waste gas stream at a regeneration pressure between 2 and 10 bar absolute.

The PSA method is very frequently used for separating and for purifying gases.

In the case of the treatment of hydrogen-rich gases, this method is suitable for generating a pure hydrogen stream, typically with purity above 99% by volume, and a hydrogen-poor waste gas concentrating the other species present in the initial gas mixture to be purified.

Any PSA method is characterized by two main steps, as follows:

- an adsorption phase in which the feed gas is contacted with one or more beds each containing one or more adsorbents, at an adsorption pressure (P) at which the compounds other than hydrogen are adsorbed and hence retained on the solid adsorbent(s). The gas leaving the bed is purified hydrogen which is produced at a production pressure (P') close to the adsorption pressure (P); generally, the difference between these pressures P and P' is less than 1 bar.
- a desorption phase in which the adsorbent(s) is(are) scavenged by an elution gas other than the feed gas at a regeneration pressure (P"), such as: P"<P, at which the adsorbed compounds are desorbed, then recovered downstream of the adsorbent bed at this regeneration pressure (P"). On completion of this desorption step, the adsorbent can undergo a new adsorption step.

The lower the regeneration pressure (P"), the more efficient the desorption of the undesirable compounds. This regeneration pressure (P") therefore has a strong impact on the purity of the hydrogen produced, on the hydrogen recovery rate, and on the quantity of adsorbent needed.

In practice, the adsorbents generally used for treating $H_2$/hydrocarbon mixtures require a regeneration pressure (P") between 1.5 and 2 bar absolute, but always less than 3 bar absolute. This is because, if the regeneration pressure exceeds this maximum value, the species heavier than propane, which are always present in the gas stream to be purified, are permanently adsorbed on the adsorbent and rapidly poison it.

Moreover, at all petrochemical facilities, the hydrocarbon-rich waste gases from all the units, and in particular those from the hydrogen purification units, cannot be released to the atmosphere. They are collected on a fuel gas network which supplies the various burners of the facility.

The pressure of this network (P''') is generally between 4 and 7 bar absolute, that is, always above 3 bar absolute in practice.

This explains why, due to the difference in pressure that exists, the waste gases from PSA units can never be sent directly to the fuel network of a petrochemical facility.

Many alternatives have already been proposed to try to solve this problem.

According to one known solution, the waste gas leaving the PSA unit is compressed by a rotating machine, such as a gas compressor, thereby raising the pressure of this waste gas from the pressure P" to the pressure P''' in order to introduce it subsequently into the fuel network of the petrochemical facility.

According to another known solution, the burners of several furnaces are replaced to permit the combustion of the gas at the pressure P''', which avoids having to compress it, as in the previous case.

However, these two known solutions are very costly because they generally increase the total cost of hydrogen purification by a factor of 1.5 to 3.

The problem which accordingly arises is to be able to purify the hydrogen-rich gases economically, in particular those containing at least one heavy hydrocarbon species of the $C_3$+ type, that is, in which the number of carbon atoms is 3 or more, and without facing the problems encountered in the prior art.

SUMMARY

The solution of the invention is accordingly a PSA method for separating a gas mixture containing hydrogen ($H_2$) and impurities selected among the hydrocarbons ($C_nH_m$), in which:

a) the gas mixture to be purified is contacted with a first adsorbent containing at least a silica gel and with a second adsorbent containing at least an activated charcoal in order to adsorb on said adsorbents at least a portion of the impurities present in the gas mixture to be treated,
b) hydrogen is produced at a production pressure (P'),
c) at least a portion of the impurities adsorbed in step (a) is desorbed,
d) a waste gas stream is produced containing said impurities desorbed in step (c), said waste gas stream being produced at a regeneration pressure (P") between 2 and 10 bar absolute.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DESCRIPTION OF PREFERRED EMBODIMENTS

Figure 1:
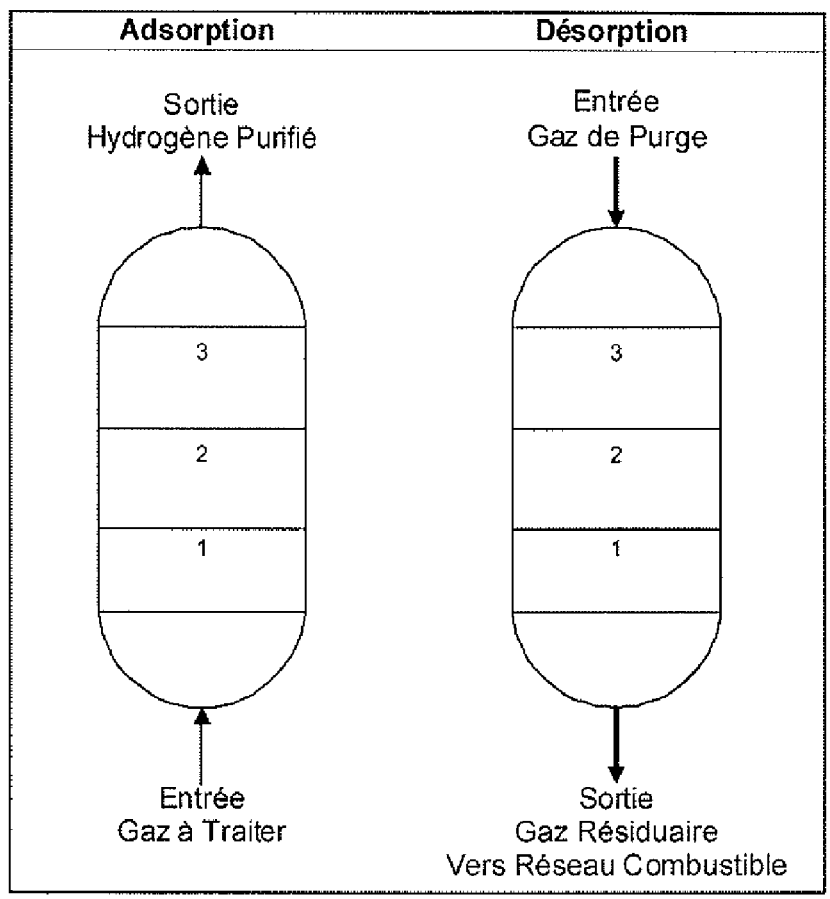
FIG. 1 illustrates one embodiment of the adsorption and desorption process according to the invention.

The invention is provides a PSA method for separating a gas mixture containing hydrogen ($H_2$) and impurities selected among the hydrocarbons ($C_nH_m$), in which:

a) the gas mixture to be purified is contacted with a first adsorbent containing at least a silica gel and with a second adsorbent containing at least an activated charcoal in order to adsorb on said adsorbents at least a portion of the impurities present in the gas mixture to be treated,
b) hydrogen is produced at a production pressure (P'),
c) at least a portion of the impurities adsorbed in step (a) is desorbed, d) a waste gas stream is produced containing said impurities desorbed in step (c), said waste gas stream being produced at a regeneration pressure (P''') between 2 and 10 bar absolute.

Depending on the case, the method of the invention can comprise one or more of the following technical features:

the regeneration pressure (P''') is 3 bar absolute or more,
the regeneration pressure (P''') is 4 bar absolute or more,
the waste gas stream is produced directly at said regeneration pressure (P''') without a prior step of compression of this waste gas,
the gas in step (a) is at an adsorption pressure (P) between 20 and 50 bar absolute,
prior to step (a), the gas mixture to be purified is contacted with an activated alumina type adsorbent,
the activated alumina has a surface area per unit mass of at least 200 m$^2$/g, preferably above 270 m$^2$/g, and a pore volume above 0.25 cm$^3$/g,
the silica gel has a surface area per unit mass above 400 m$^2$/g, preferably above 600 m$^2$/g, and a pore volume above 0.25 cm$^3$/g,
the activated charcoal has a surface area per unit mass above 600 m$^2$/g, preferably above 850 m$^2$/g, and a pore volume above 0.25 cm$^3$/g,
in step b), hydrogen is produced at a production pressure (P') between 20 and 50 bar absolute and/or with a purity of at least 98.5 vol %,
the waste gas stream produced in step d) is sent to a fuel network of a petrochemical facility, particularly a refinery,
the waste gas stream produced in step d) is sent to a line in which a gas or a gas mixture flows at a pressure between 3 and 8 bar absolute,
the gas mixture to be purified contains, in addition, impurities selected among $CO_2$, water vapor, N2 and CO,
the gas mixture to be purified contains hydrocarbons with at least 3 carbon atoms in their hydrocarbon chain, preferably hydrocarbons selected among propane, propene, butane, butene, pentane, hexane, benzene, toluene, xylene and their isomers,
the gas mixture to be purified is first contacted with the silica gel and then with the activated charcoal,
the gas mixture to be purified is produced by a catalytic reforming unit.

Thanks to the use of a particular combination of a plurality of adsorbent beds, the invention makes it possible to carry out the regeneration step at high pressure and, more precisely, at a pressure greater than or equal to that of the fuel network of the petrochemical facility on which the PSA unit is installed.

Figure 2:
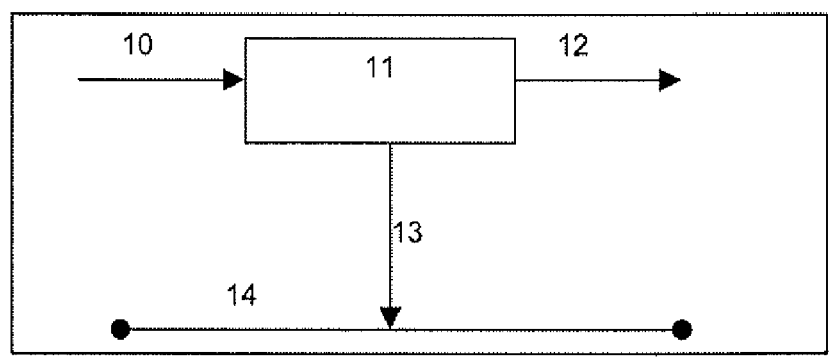
FIG. 2 illustrates the integration of the invention at a petrochemical facility.

Thus, FIG. 2 shows the integration of this PSA method at a petrochemical facility. The feed gas to be treated 10 is introduced into the PSA 11 to be purified therein by the method of the invention and thereby to recover a purified hydrogen stream 12. Moreover, the waste gas 13 is also recovered and can be sent, according to the invention, at a regeneration pressure between 3 and 10 bar absolute for example, to the fuel gas network 14 of the petrochemical facility.

The invention allows a significant increase in the regeneration pressure of the adsorbent in the PSA method and thereby serves to avoid the very frequent and very costly step of compression of the waste gas leaving the PSA.

The respective quantities of charcoal and silica gel are selected according to the $C_3+$ content of the feed gas, the pressure P of the feed gas, the pressure P''' of the waste gas, and the desired purity of the hydrogen produced.

Preferably, the adsorbent of the invention comprises a bed of activated alumina at the inlet, which is followed by a bed of silica gel and a bed of activated charcoal in the proportions given below and as shown in the figure appended hereto.

In fact, as shown in FIG. 1:
the alumina layer 1, located on the feed side (inlet) of the adsorption zone, accounts for 0 to 10% by volume of the total quantity of adsorbent,
the silica gel layer 2, sandwiched between the two layers of alumina 1 and activated charcoal 3, accounts for 30 to 70% of the total quantity of adsorbent, and
the activated charcoal layer 3, located on the production side (outlet) of the adsorption zone, accounts for 30 to 70% of the total quantity of adsorbent.

The gas to be purified therefore successively passes through the alumina layer 1, the silica gel layer 2 and the activated charcoal layer 3.

The surface area per unit mass of the activated alumina used must be at least 200 m$^2$/g, preferably above 270 m$^2$/g, with a pore volume above 0.25 cm$^3$/g. It can possibly be doped with an alkaline compound suitable for reversibly adsorbing the carbon dioxide ($CO_2$). The beads are between 1 and 5 mm in size, preferably between 2 and 3.5 mm.

The silica gel used has a surface area per unit mass above 400 m$^2$/g, preferably above 600 m$^2$/g, and a pore volume above 0.25 cm$^3$/g. The beads are between 1 and 5 mm in size, preferably between 2 and 3.5 mm. This silica gel has a Henry constant at least two times smaller than that of the activated charcoal with which it is combined, and which has the following properties:

The activated charcoal has a surface area per unit mass above 600 m$^2$/g, preferably above 850 m$^2$/g, and a pore volume above 0.25 cm$^3$/g. The particles must be between 1 and 5 mm in size.

The method of the invention can be put into practice in PSA units using 3 to 20 adsorbers, preferably about 6 to 12.

EXAMPLE

The effectiveness of the method of the invention was confirmed during the purification of a hydrogen stream from a catalytic reforming unit located at a refining facility, the composition and properties of which are given in Table I below.

TABLE I

| Feed Gas | Properties |
|---|---|
| Adsorption pressure | 26 bar abs |
| Temperature | 40° C. |
| Components | Molar composition |
| $H_2$ | 75% |
| $CH_4$ | 11% |
| $C_2H_6$ | 7% |
| $C_3H_8$ | 4% |
| $C_4H_{10}$ | 2.5% |
| $C_5+$ | 0.5% |

The gas stream was subjected to purification by the PSA method using a combination of adsorbents according to the invention and, for comparison, a succession of adsorbents according to the prior art (charcoal only).

The operating conditions of the conventional PSA unit were as follows:
adsorption pressure: 26 bar absolute number of adsorbers: 6
number of balancings: 3
gas temperature: 40° C.
silica gel: marketed by Engelhard under the reference Sorbead
activated charcoal: marketed by Norit under the reference R3 Extra
proportion of silica gel/charcoal: 50/50 (0/100 according to the prior art)

The results obtained (purity, recovery rate) are given in Table II below.

TABLE II

|  | Conventional Adsorbents Charcoal | | Adsorbents of the invention 50% Silica gel + 50% Charcoal | |
|---|---|---|---|---|
| Regeneration Pressure | 1.6 bar abs | 6 bar abs | 1.6 bar abs | 6 bar abs |
| Purity of hydrogen produced, vol % | 99.5% | Operation impossible | 99.5 | 99.5 |
| Recovery rate of hydrogen in pure product | 90% | Incomplete desorption of $C_{3+}$ compounds | 89% | 65% |
| Throughput of $H_2$ produced per volume of adsorbent | 688 $Sm^3/h/m^3$ | | 656 $Sm^3/h/m^3$ | 142 $Sm^3/h/m^3$ |

As shown by Table II, only the sound combination of adsorbents according to the invention can serve to produce hydrogen with a purity of 99.5% while producing the waste gas at a pressure of 6 bar absolute without a compression step. In the case of a charcoal according to the prior art, the desorption of the heavy hydrocarbons ($C_3+$) is incomplete. The adsorbent is very quickly contaminated by the impurities present in the feed gas, which prevents maintaining a product purity above 99.5% over time.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method which may be used for a PSA separation of a gas mixture, wherein said gas mixture comprises hydrogen and impurities which comprise at least one hydrocarbon ($C_nH_m$), comprising:
   a) contacting said gas mixture with a first adsorbent, wherein said first adsorbent comprises a silica gel, and a second adsorbent, wherein said second comprises an activated charcoal;
   b) adsorbing at least a portion of the impurities of said gas mixture with said first and said second adsorbents;
   c) producing hydrogen at a production pressure (P');
   d) desorbing at least a portion of said impurities from said adsorbents; and
   e) producing a waste gas stream, wherein said waste gas stream has a regeneration pressure (P") between about 2 bar absolute and about 10 bar absolute and wherein said waste gas stream further comprises said impurities, wherein said regeneration pressure (P") is greater than or equal to a pressure of a fuel network of a petrochemical facility on which the PSA unit is installed.

2. The method of claim 1, wherein said regeneration pressure (P") is greater than 3 bar absolute.

3. The method of claim 1, wherein said regeneration pressure (P") is greater than 4 bar absolute.

4. A method which may be used for a PSA separation of a gas mixture, wherein said gas mixture comprises hydrogen and impurities which comprise at least one hydrocarbon ($C_nH_m$), comprising:
   a) contacting said gas mixture with a first adsorbent, wherein said first adsorbent comprises a silica gel, and a second adsorbent, wherein said second comprises an activated charcoal;
   b) adsorbing at least a portion of the impurities of said gas mixture with said first and said second adsorbents;
   c) producing hydrogen at a production pressure (P');
   d) desorbing at least a portion of said impurities from said adsorbents; and
   e) producing a waste gas stream, wherein said waste gas stream has a regeneration pressure (P") between about 2 bar absolute and about 10 bar absolute and wherein said waste gas stream further comprises said impurities, further comprising producing said waste gas stream at said regeneration pressure (P") in the absence of a compression means, wherein said genreation regeneration pressure (P") is greater than or equal to a pressure of a fuel network of a petrochemical facility on which the PSA unit is installed.

5. The method of claim 1, wherein said gas mixture comprises an adsorption pressure (P) between about 20 bar absolute and about 50 bar absolute.

6. The method of claim 1, further comprising contacting said gas mixture with an activated alumina adsorbent prior to contact with said first and said second adsorbents.

7. The method of claim 6, wherein said activated alumina comprises:
   a) a surface area per unit mass greater than about 200 $m^2/g$; and
   b) a pore volume greater than about 0.25 $cm^3/g$.

8. The method of claim 7, wherein said surface area is greater than about 270 $m^2/g$.

9. The method of claim 1, wherein said silica gel comprises:
   a) a surface area per unit mass greater than about 400 $m^2/g$; and
   b) a pore volume greater than about 0.25 $cm^3/g$.

10. The method of claim 9, wherein said surface area is greater than about 600 $m^2/g$.

11. The method of claim 1, wherein said activated charcoal comprises:
   a) a surface area per unit mass greater than about 600 $m^2/g$; and
   b) a pore volume greater than about 0.25 $cm^3/g$.

12. The method of claim 11, wherein said surface area is greater than about 850 $m^2/g$.

13. The method of claim 11, wherein said production pressure (P') is between about 20 bar absolute and 50 bar absolute.

14. The method of claim 1, wherein said hydrogen produced comprises a purity greater than about 98.5 vol %.

15. The method of claim 13, wherein said hydrogen produced comprises a purity greater than about 98.5 vol %.

16. The method of claim 1, further comprising sending said waste gas stream to the fuel network of the petrochemical facility.

17. The method of claim 16, wherein said petrochemical facility comprises a refinery.

18. The method of claim 1, further comprising sending said produced waste gas stream to a pipeline network, wherein said network comprises a gas flowing at a pressure between about 3 bar absolute and about 8 bar absolute.

19. The method of claim 1, wherein said gas mixture further comprises at least one member selected from the group consisting of:
 a) carbon dioxide;
 b) water;
 c) nitrogen; and
 d) carbon monoxide.

20. The method of claim 1, wherein said gas mixture comprises hydrocarbons with at least 3 carbon atoms in the hydrocarbon chain.

21. The method of claim 20, wherein said hydrocarbons comprise at least one member selected from the group consisting of:
 a) propane;
 b) propene;
 c) butane;
 d) butene;
 e) pentane;
 f) hexane;
 g) benzene;
 h) toluene;
 i) xylene; and
 j) isomers thereof.

22. The method of claim 1, wherein said gas mixture is contacted with said first adsorbent before being contacted with said second adsorbent.

23. The method of claim 1, wherein said gas mixture is produced with a catalytic reforming means.

24. A method which may be used for a PSA separation of a gas mixture, wherein said gas mixture comprises hydrogen and impurities which comprise at least one hydrocarbon ($C_nH_m$), comprising:
 a) contacting said gas mixture with a first adsorbent, wherein said first adsorbent comprises an adsorbent which adsorbs at least one hydrocarbon ($C_nH_m$), and a second adsorbent, wherein said second comprises an activated charcoal;
 b) adsorbing at least a portion of the impurities of said gas mixture with said first and said second adsorbents;
 c) producing hydrogen at a production pressure (P');
 d) desorbing at least a portion of said impurities from said adsorbents; and
 e) producing a waste gas stream, wherein said waste gas stream has a regeneration pressure (P") between about 2 bar absolute and about 10 bar absolute and wherein said waste gas stream further comprises said impurities, wherein said regeneration pressure (P") is greater than or equal to a pressure of a fuel network of a petrochemical facility on which the PSA unit is installed.

25. A method which may be used for a PSA separation of a gas mixture, wherein said gas mixture comprises hydrogen and impurities which comprise at least one hydrocarbon (CnHm), comprising:
 a) contacting said gas mixture with an activated alumina adsorbent;
 b) contacting said gas mixture with a first adsorbent, wherein said first adsorbent comprises a silica gel, and a second adsorbent, wherein said second comprises an activated charcoal;
 c) adsorbing at least a portion of the impurities of said gas mixture with said first and said second adsorbents;
 d) producing hydrogen at a production pressure (P');
 e) desorbing at least a portion of said impurities from said adsorbents;
 f) producing a waste gas stream, wherein said waste gas stream has a regeneration pressure (P") above about 3 bar absolute and wherein said waste gas stream further comprises said impurities; and
 g) sending said waste gas stream to the pipeline network of a fuel network of a petrochemical facility, wherein said pipeline network comprises a gas flowing at a pressure above about 3 bar absolute, wherein said regeneration pressure (P") is greater than or equal to the pressure of the pipeline network.

* * * * *